(12) United States Patent
Osterbrink et al.

(10) Patent No.: US 7,186,325 B2
(45) Date of Patent: Mar. 6, 2007

(54) PRESSURE-RESISTANT REFERENCE ELECTRODE FOR ELECTROCHEMICAL MEASUREMENTS

(75) Inventors: Ulf Paul Osterbrink, Emsdetten (DE); Rolf Thrier, Tagelswangen (CH)

(73) Assignee: Mettler-Toledo AG, Greifensee (CH)

( * ) Notice: Subject to any disclaimer, the term of this patent is extended or adjusted under 35 U.S.C. 154(b) by 592 days.

(21) Appl. No.: 10/370,460

(22) Filed: Feb. 24, 2003

(65) Prior Publication Data

US 2003/0183522 A1   Oct. 2, 2003

(30) Foreign Application Priority Data

Feb. 22, 2002   (DE) ................ 102 07 624

(51) Int. Cl.
*G01N 27/30* (2006.01)
*G01N 27/40* (2006.01)

(52) U.S. Cl. ...................... 204/408; 204/435
(58) Field of Classification Search ........ 204/408, 204/435
See application file for complete search history.

(56) References Cited

U.S. PATENT DOCUMENTS

| | | | |
|---|---|---|---|
| 2,697,070 A | 12/1954 | Arthur | |
| 3,145,158 A | 8/1964 | Matsuyama | |
| 3,616,414 A | 10/1971 | Houwelingen | |
| 3,793,176 A * | 2/1974 | Jerrold-Jones | 204/435 |
| 4,659,451 A | 4/1987 | Fujita et al. | |
| 4,818,366 A | 4/1989 | Yonco et al. | |
| 4,980,043 A | 12/1990 | Tomita et al. | |
| 5,360,529 A * | 11/1994 | Edwards et al. | 204/435 |
| 6,423,197 B1 | 7/2002 | Lenferink et al. | |

OTHER PUBLICATIONS

U.S. Appl. No. 10/025,547, filed Dec. 26, 2001, Schmitz et al.
U.S. Appl. No. 10/269,052, Oct. 11, 2002, Ries et al.
U.S. Appl. No. 10/024,386, Dec. 21, 2001, Schmitz et al.
Galster, "pH Measurement", VCH Publishers, NY, NY, pp. 104-108 (1991).
Submersible Flat Surface Combination pH Electrode, Bulletin 408, Sensorex (1980).

* cited by examiner

*Primary Examiner*—Nam Nguyen
*Assistant Examiner*—Anthony Fick
(74) *Attorney, Agent, or Firm*—Buchanan Ingersoll & Rooney

(57) ABSTRACT

A pressure-resistant reference electrode for electrochemical measurements includes both a half cell and a primary current bridge, provided for closing an electrochemical contact between the half cell and a measurement medium, which current bridge contains a primary electrolyte. The half cell has a reference electrolyte and a lead-off element, dipped into the reference electrolyte, which are disposed in a half-cell chamber that is provided with a primary junction leading to the primary current bridge and is otherwise embodied as medium-proof. The half-cell chamber furthermore has a flexible wall region, which is embodied such that a pressure difference between the primary current bridge and the half cell can be compensated for essentially without convection by the primary junction.

22 Claims, 4 Drawing Sheets

PRESSURE-RESISTANT REFERENCE ELECTRODE FOR ELECTROCHEMICAL MEASUREMENTS

BACKGROUND

RELATED APPLICATIONS

This application claims priority under 35 U.S.C. §§119 and 365 to German Patent Application No. 10207624.3 filed in Germany on Feb. 22, 2002, the entire content of which is hereby incorporated by reference.

FIELD OF THE INVENTION

The invention relates to a pressure-resistant reference electrode.

BACKGROUND INFORMATION

Reference electrodes are known to be intended for furnishing a constant reference potential for electrochemical measurements, for instance for measuring pH values, redox potentials, or ion concentrations, or for amperometric measurements. Currently used reference electrodes include a half cell with a lead-off element and a reference electrolyte, and the half cell can in particular be designed as an electrode of a second type (such as Ag/AgCl, Hg/Hg$_2$Cl$_2$, or thalamide), or as a redox electrode (such as iodine/iodide). Because of their mode of operation, these half cells are affected in such a way by the invasion of interfering substances—also called electrode poisons—that can penetrate them particularly from the measurement medium, that the half cell potential is interfered with irreversibly, and the reference electrode cannot be used anymore.

For electrodes of the second type, the electrode poisons include salts of the kind that, with the potential-determining cation, produce a salt that is more insoluble than the one present in the reference system. For instance, the contact of an Ag/AgCl system with sulfide solutions causes Ag$_2$S to precipitate out, and a half cell potential of Ag/Ag$_2$S develops, which deviates considerably from the original Ag/AgCl potential used as a reference. Diluting agents, however, can also serve as electrode poisons, since in the Ag/AgCl reference electrode, for instance, the half cell potential according to Nernst depends on the anion concentration (Cl$^-$) as follows:

$$E=E°-RT/zF \ln a_{Cl^-} \quad [1]$$

In redox electrodes, the influence of dilution is negligible or is at least reduced because the potential depends on the activity ratio of the applicable redox pairs, which varies only slightly if at all as a rule upon dilution:

$$E=E°+RT/zF \ln [Ox]/[Red] \quad [2]$$

However, even with redox electrodes, certain substances can act as electrode poisons, since for instance hypochlorite, chlorates, bleaching agents, and so forth irreversibly interfere with the redox potential upon penetration into the potential-determining half cell.

Since in a reference electrode an electrochemical contact is compulsory between the half cell and the applicable measurement medium, on the one hand an exchange of charge carriers between the reference electrolyte and the measurement medium must be assured, but on the other, a penetration of electrode poisons into the reference electrolyte must be avoided. Thus a compromise must be made, and by structural provisions and a suitable choice of the type of reference and the electrolyte, a reference electrode must be found in which there is as little penetration by electrode poisons as possible, yet an adequate ion flow between the half cell and the measurement medium is still possible. To that end, it is known to install a transition—also known as a "liquid junction" and referred to here as a "junction" between the half cell and the measurement medium, the junction being embodied for instance as a porous diaphragm. It is also known to dispose a current bridge—also known as an electrolyte bridge—between the half cell and the measurement medium, in which case there is a total of two junctions between the measurement medium and the reference electrolyte.

The prevention of electrode poisoning is especially difficult if a reference electrode is used at an elevated pressure—compared to the pressure prevailing in the electrode. Because of the pressure gradient, convection of the measurement medium into the reference electrode occurs, which intrinsically means that electrode poisons in the measurement medium are carried into the reference electrode as well.

German Patent Disclosure DE 34 11 800 A1 describes a reference electrode of this generic type, which has both a half cell and a primary current bridge, the latter being filled with a primary electrolyte and intended to close an electrochemical contact between the half cell and a measurement medium. The half cell contains a reference electrolyte and a lead-off element dipped into it, which are disposed in a half-cell chamber. The half-cell chamber is formed by a glass tubule, which on its lower end has a primary junction, in the form of a first diaphragm, leading to the primary current bridge. The primary current bridge is located in a housing that is intended for being dipped in a measurement medium and that has a measurement junction which assures the electrochemical contact between the primary electrolyte and the measurement medium. Because the measurement junction of DE 34 11 800 A1 is formed by a second diaphragm supported on a flexible membrane, a buildup of pressure differences between the measurement medium and the primary electrolyte is avoided, thus preventing convection through the measurement junction. However, the membrane is not mechanically stable enough to compensate also for large pressure differences and to mechanically withstand major deformations, and it functions only in combination with a completely filled reference chamber, in which only hydraulic pressures are compensated for, and thus only slight deformations can be withstood by the membrane. Moreover, with a reference electrode of DE 34 11 800 A1, a pressure equalization can indeed be attained between the measurement medium and the primary electrolyte, but not between the primary electrolyte and the reference electrolyte. As a result, a pressure gradient ensues between the primary electrolyte and the reference electrolyte, which causes an extremely unwanted convection through the primary junction. In particular, this can cause poisoning of the half cell and thus a change in the half cell potential.

U.S. Pat. No. 5,360,529 describes a reference electrode with a half cell and a primary current bridge, which are filled with suitable gel electrolytes and are surrounded by an outer housing. The purpose of these casings is to improve the mechanical stability of the intrinsically not very mechanically stable gel electrolyte. As the housing material, besides glass which is typical for that purpose, polyethylene is also mentioned. U.S. Pat. No. 5,360,529 does not provide any teaching whatever about any mechanical pressure equalization between the measurement medium and the interior of the electrode housing. In particular, it provides no teaching on handling in order to avoid unwanted convection into or out of the half cell.

SUMMARY OF THE INVENTION

The present invention is directed to a reference electrode which does not have the aforementioned disadvantages and which in particular can be used as a pressure-resistant reference electrode for electrochemical measurements.

The reference electrode includes both a half cell and a primary current bridge, provided for closing an electrochemical contact between the half cell and a measurement medium, which current bridge contains a primary electrolyte. The half cell has a reference electrolyte and a lead-off element, dipped into the reference electrolyte, which are disposed in a half-cell chamber that is provided with a primary junction leading to the primary current bridge and is otherwise embodied as medium-proof. Because the half-cell chamber furthermore has a flexible wall region, which is embodied such that a pressure difference between the primary current bridge and the half cell essentially can be compensated for without convection through the primary junction, convection through the primary junction is avoided. Accordingly, in particular the penetration of substances that cause an unwanted change in the electrochemical potential of the half cell is prevented.

The half-cell chamber can be disposed inside the primary current bridge. In particular, the primary current bridge can be accommodated in a comparatively robust outer housing, which furthermore includes the half-cell chamber as well. Among other goals, it is thus attained that the flexible wall region of the half-cell chamber is located in the interior of the housing.

In principle, various embodiments for the primary junction are possible. For example, the primary junction can be formed by a diaphragm. In particular, the diaphragm can be embodied flexibly and can thus form the flexible wall region, or a part of it.

Because the half-cell chamber contains a secondary current bridge disposed between the half cell and the primary junction, a better separation can be achieved between the potential-determining half cell and the measurement medium, making an unwanted contamination of the half cell more difficult. The flexible wall region of the half cell can be provided in a portion of the half cell in which the secondary current bridge is disposed. The flexible wall region can be formed by a hose, or conversely it can be formed by a film.

The reference electrode can be suitable for production by thin-film technology; thus a very flat reference electrode can in particular be realized. The reference electrode can be produced by modular construction, which among other things makes it possible to adapt it to specific requirements of the intended area of use. It can prove advantageous if the lead-off element is embodied as a conductor track.

To delay contamination of the potential-determining half cell as long as possible, rapid diffusion of the measurement medium up to the half cell should be avoided as much as possible. In particular, the half-cell chamber and/or the primary current bridge can be equipped with a meandering diffusion path, which in the final analysis is equivalent to lengthening to diffusion path without an unwanted increase in the external dimensions. It can also be provided that one or more of the electrolytes are in gel form, which reduces the diffusion speed.

The primary junction can be embodied as a highly compacted junction, so that convection through the primary junction is maximally avoided.

BRIEF DESCRIPTION OF THE DRAWINGS

Exemplary embodiments of the invention are described in further detail below in conjunction with the drawings, which show.

DESCRIPTION OF THE PREFERRED EMBODIMENTS

Figure 1:
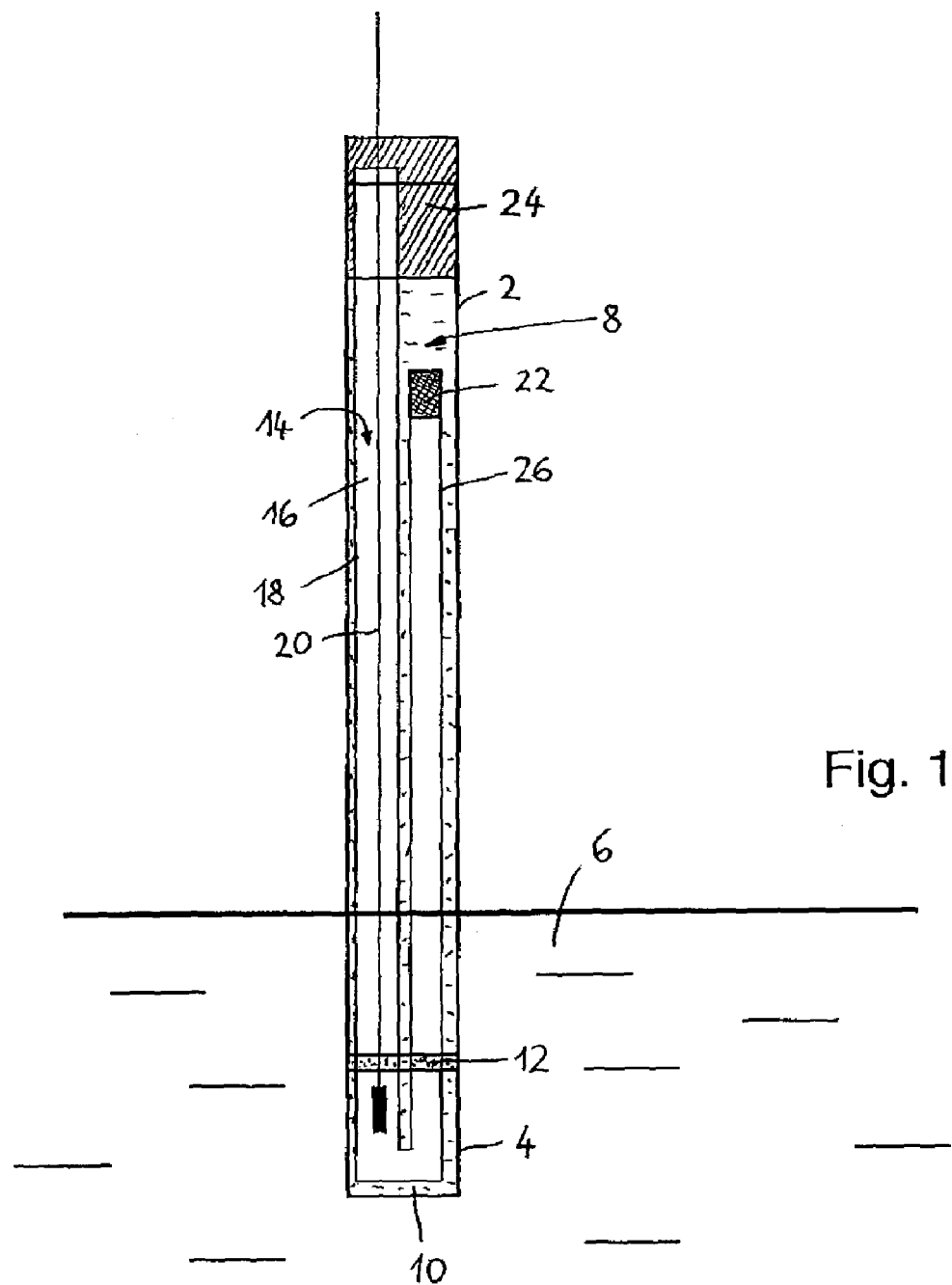
FIG. 1, an exemplary reference electrode, in longitudinal section.

The reference electrode shown in FIG. 1 has a tubular housing 2, whose lower end 4, in the example shown, is dipped into a measurement medium 6. A primary current bridge 8 is formed by a primary electrolyte 10, contained in the housing 2, which is in electrochemical contact with the measurement medium 6 via a measurement junction 12 disposed on the lower end 4. Serving here as the measurement junction 12 is an annular porous diaphragm. The reference electrode also includes an electrochemical half cell 14, acting as a reference element, which includes a half-cell chamber 18, filled with a reference electrolyte 16, and a lead-off element 20 dipped into the reference electrolyte 16. In the example shown, the half cell 14 is embodied as an electrode of the second type, for instance as a silver/silver chloride electrode, in which the reference electrolyte 16 is saturated with AgCl. The half-cell chamber 18 has a primary junction 22, by which an electrochemical contact between the reference electrolyte 16 and the primary electrolyte 10 is assured. Otherwise, the half-cell chamber 18 is embodied as medium-proof; the lead-off element 20 is extended out of the half-cell chamber 18 through an upper closure part 24 of the reference electrode. With the arrangement shown, an electrochemical contact between the half cell 14 and the measurement medium 6 is created in a manner known per se.

The half-cell chamber 18 is formed by an elastic hose, which is completely filled with the reference electrolyte 16, and whose flexible wall 26 creates a variable internal volume of the half-cell chamber 18, so that a pressure difference between the primary current bridge and the half cell can be compensated for essentially without convection through the primary junction, for example, the flexible wall can be configured such that convection either does not occur, or is at or below an acceptable limit for the intended application.

For the half-cell chamber 18, a hose material with a maximum hardness of 70 (Shore A) is used. The hose can be as thin-walled as possible, so that as complete as possible a pressure transfer to the electrolytes located in the half-cell chamber is brought about. For a predetermined wall thickness, using a hose with a non-circular cross section makes it possible to achieve better deformability and thus a better pressure transfer. For a circular silicone hose with a Shore A hardness of 50 and a temperature resistance up to 200° C., good results have been attained with a wall thickness that is a maximum of one-third of the outer diameter of the hose, for instance with an outer diameter of 1.6 mm and a wall thickness of 0.4 mm. Other suitable flexible materials are elastic PVC (maximum 60° C.), all rubbers, such as NBR (maximum 120° C.), HNBR (maximum 150° C.), natural rubber (maximum 80° C.), chlorine rubbers, fluorosilicone elastomers, butadiene rubber, and other known elastomers. The temperature-resistant materials such as HNBR and silicone are in particular also suitable for sterilizable reference electrodes. Since over the course of time the electrolyte located closest to the measurement medium takes on the composition of the measurement medium, elastomers such as fluorosilicone, fluororubbers (Viton, Kalretz) that are resistant to chemicals can be used when particularly aggressive measurement media are involved. The flexible wall region of the reference electrode can also be formed of a thermoplastic elastomer, and because of the heat-deformability, particular shapings can be attained as needed. Since such materials are as a rule less elastic than the materials first named above, thinner wall thicknesses can be provided in order to assure a pressure transfer.

In the example shown, the primary junction 22 comprises a ceramic diaphragm that has been lined predominantly with a hydrophilic layer, such as an acryl derivative gel with a small proportion of water, and has thus been made into a highly compacted internal transition. Advantageously, the half-cell chamber 18 is made as long as possible, so as to lengthen the poisoning distance to the half cell 14 as much as possible and thus achieve a longer service life of the electrode. Besides a long diffusion path, gelling of the reference electrolyte can also lower the diffusion coefficients considerably for ions migrating in it. These provisions lead to a drastically longer length of use of the reference electrode, which is especially advantageous with critical measurement media above all.

In the example shown, the elastic half-cell chamber 18 is embedded in the primary electrolyte 10, which in turn is surrounded by the housing 2 made of a sturdy glass or plastic. As the measurement junction, instead of the porous ceramic diaphragm 12, a diaphragm of porous, dirt-repellent Teflon or some other material suitable for the purpose can be used.

The reference electrode described is pressure-resistant to the extent that any overpressure that may arise in the primary current bridge 8 is absorbed by the elastically embodied half-cell chamber 18 and transferred to the reference electrolyte 16. As a result, there is a decrease in the volume of the half-cell chamber 18, until the internal pressure in the reference electrolyte 16 is equal to the external pressure acting on the half-cell chamber 18. Because of this pressure equalization, a pressure gradient is not established at the primary junction 22, and so an unwanted pressure-gradient-driven convection through the primary junction 22 is avoided.

The volumetric reduction required for the pressure equalization depends, among other factors, on how fully filled the half-cell chamber 18 is, and in particular it is of significance that gases are substantially more-compressible than other media. If the half-cell chamber 18 is essentially completely filled (e.g., completely filled or at least half filled) with a reference electrolyte 16 that is in liquid or gel form or in any case solid form, then for the pressure equalization a substantially lesser volumetric reduction is required than if an air pocket or gas pocket is present in the half-cell chamber 18. Precisely by the use described here of a flexible hose, it is possible by the choice of a sufficiently high ratio of the hose length to the hose diameter to achieve a pressure equalization and thus pressure resistance of the reference electrode even if there is a relatively large volume of gas or air in the half-cell chamber 18.

To achieve the most constant possible potential of the reference electrode, the composition of the primary electrolyte should remain as constant as possible over the length of use of the reference electrode. Contamination of the primary electrolyte from electrode poisons from the measurement medium can be reduced somewhat by designing the measurement junction as a porous diaphragm, which makes convection out of the measurement medium somewhat more difficult, and/or by filling the interior of the primary current bridge 8 completely with the primary electrolyte, which allows only a hydraulic compression of the primary electrolyte and thus dictates only a slight volumetric flow through the primary junction. Alternatively, the measurement junction, like the primary junction described here, can be embodied as a highly compacted transition, as a result of which convection is largely avoided and thus substantially better protection against an unwanted penetration of substances from the measurement medium is achieved. However, this is known to cause certain incorrect potentials at the measurement junction, which vary depending on the measurement medium.

A silver-free electrolyte can-be used as the primary electrolyte, to preclude any precipitation of silver salt at the measurement junction. If the half cell contains a silver/silver chloride electrode, then a chloride-free primary electrolyte can furthermore be used, to preclude silver chloride precipitation at the primary junction; in that case, the primary electrolyte can be selected such that the least possible diffusion potentials occur at the primary junction, which is successfully achieved with $Li_2SO_4$, for instance.

To prevent bursting of the reference electrode in the event of a temperature increase with resultant hydraulic expansion of the primary electrolyte, an air cushion or a compressible foam rubber inlay can be provided in the outer electrolyte chamber; it can for instance be disposed in the upper closure part 24. If a foam rubber inlay is used, it can have closed or compressible pores, but not pores that can be filled with electrolyte.

Figure 2:
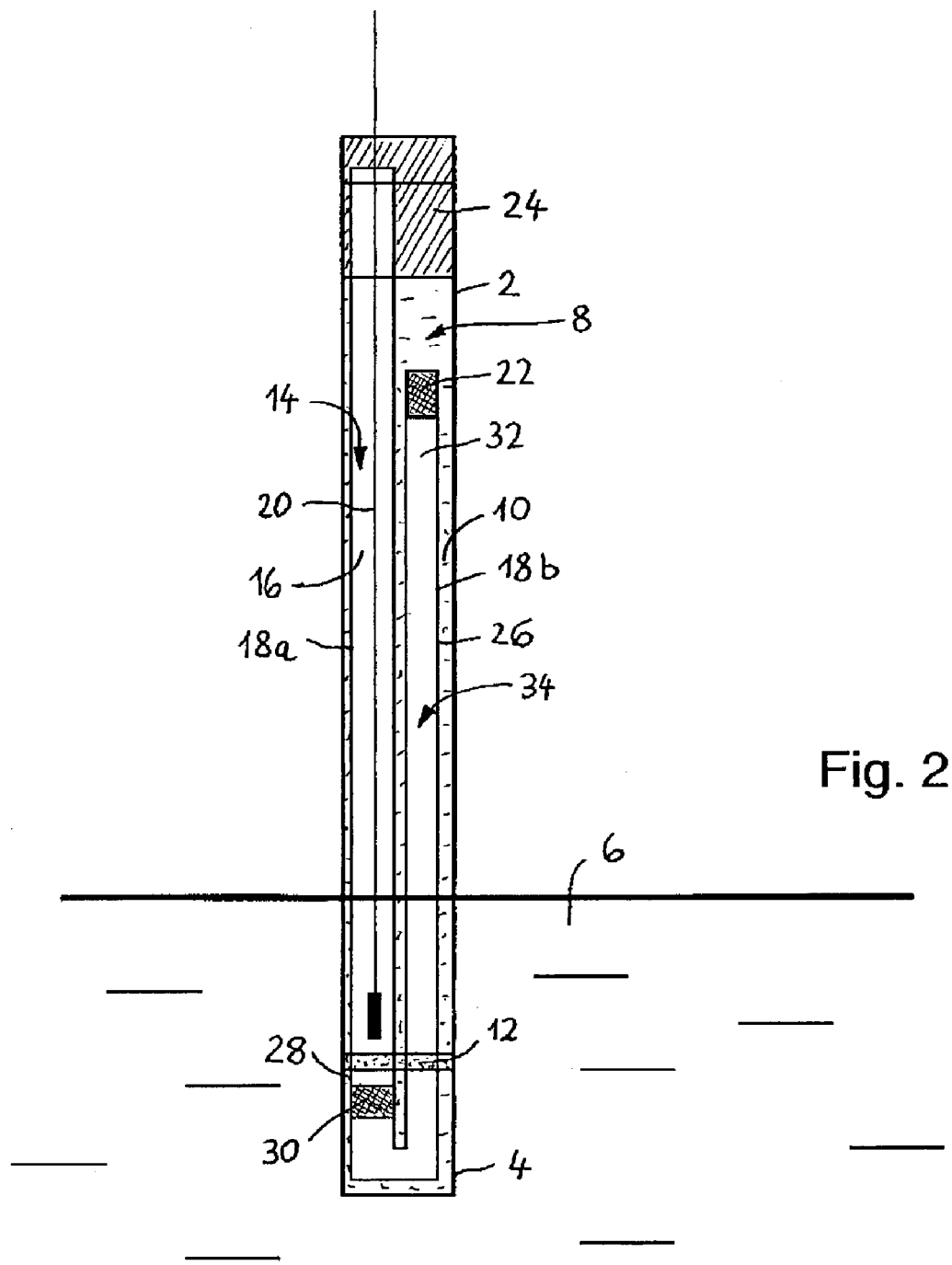
FIG. 2, an exemplary reference electrode, in longitudinal section.

The reference electrode shown in FIG. 2—also called a "triple-junction electrode"—contains a double current bridge. Like the reference electrode of FIG. 1, it has a tubular housing 2, whose lower end 4 is dipped into a measurement medium 6. A primary current bridge 8 is formed by a primary electrolyte 10 contained in the housing 2 that is in electrochemical contact with the measuring medium 6 via a measurement junction 12 disposed at the lower end 4. The reference electrode also contains an electrochemical half cell 14, acting as a reference element, with a lead-off element 20 dipped into a reference electrolyte 16. Unlike the first embodiment, however, the half cell 14 is accommodated in a rigid glass tubule 18a, onto whose distal end 28 an elastic hose 18b is placed that on its other end has a primary junction 22 discharging into the primary electrolyte 10. In other words, in this example, the half-cell chamber is formed by the rigid glass tubule 18a and the elastic hose 18b, and the latter forms a flexible wall 26 of the half-cell chamber. The glass tubule 18a is provided on its distal end 28 with a porous diaphragm or a glasswool stopper, acting as a secondary junction 30, that divides the half-cell chamber into an inner part and an outer part. The half cell 14 itself with the reference electrolyte 16 is located in the inner part, while a secondary electrolyte 32 is contained in the outer part and forms a secondary current bridge 34 disposed between the primary current bridge 8 and the half cell 14. The requisite electrochemical contact between the half cell 14 and the measurement medium 6 is thus effected via the secondary junction 30, the secondary current bridge 34, the primary junction 22, the primary current bridge 8, and the measurement junction 12.

Instead of a diaphragm, an ion-conducting polymer stopper or a semipermeable membrane can be provided in the primary junction 22. Despite the greater compaction, as a rule no problems from incorrect potentials arise from this, because the ion concentration of the primary electrolyte 10 and of the secondary electrolyte 32—although possibly markedly different—as a rule vary only quite slowly. Thus any incorrect potentials can be reliably calibrated out of existence. It is important that any pressure change occurring in the primary current bridge 8 because of a pressure equalization via the measurement junction 12 is also transferred to the secondary current bridge 34 via the flexible wall region 26, thus preventing a pressure-dictated inflow of any contaminated primary electrolyte 10 through the primary junction 22 into the half-cell chamber 18a, 18b.

Especially great durability of the reference electrode can be obtained if the innermost junction, that is, the primary junction 22 for the reference electrode of FIG. 1, or the secondary junction 30 for the reference electrode of FIG. 2, is located as far away as possible from the measurement junction 12. To avoid interfering thermodiffusion potentials and to attain faster temperature adaptation to the temperature of the measuring medium 6, the half cell 14 that actually determines the potential can be located in a region of the housing 2 that is typically surrounded by the measurement medium 6 during measurements.

In the reference electrode shown in FIG. 2, if desired, the primary electrolyte and the secondary electrolyte can be different. In another advantageous application, a catcher cartridge for silver or mercury ions (as described in European Patent Disclosure EP 0 541 739 B1, for instance) can also be accommodated in the region of the hose.

Figure 3:
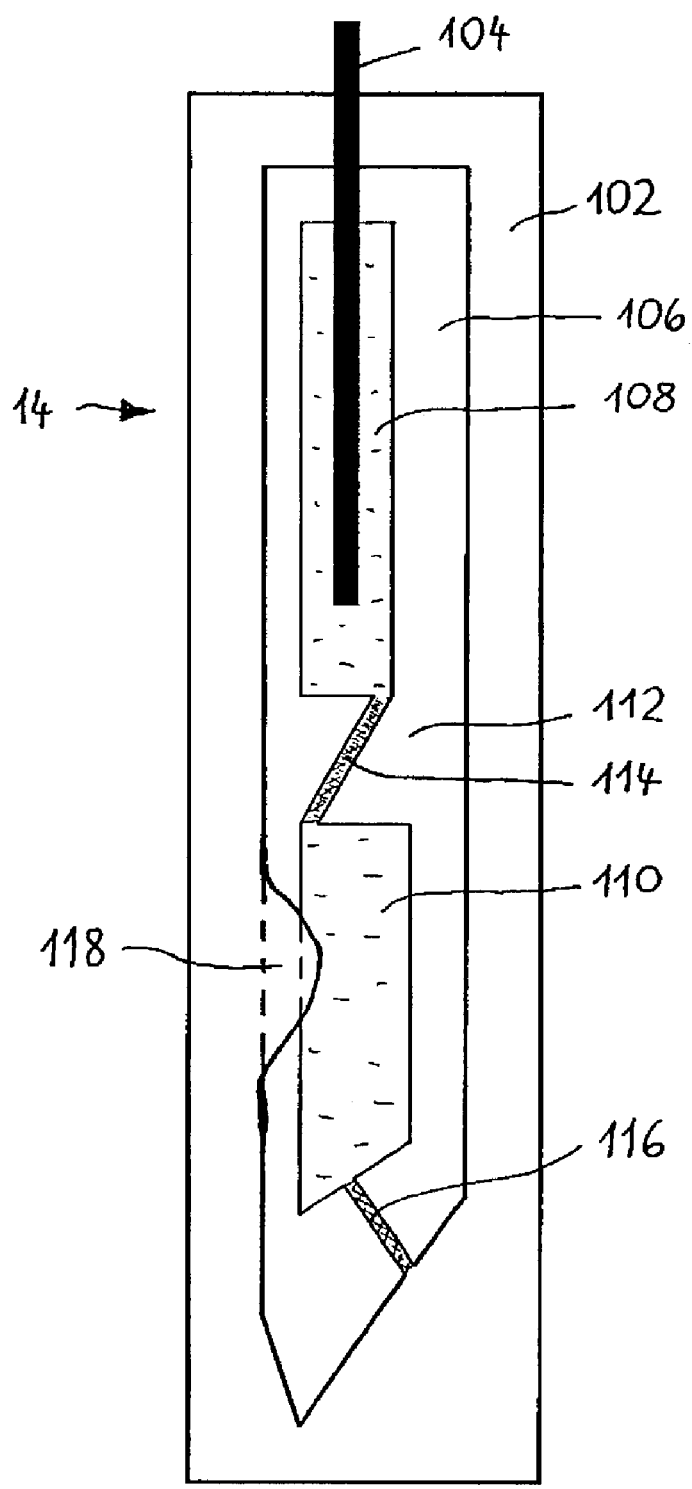
FIG. 3, an exemplary reference electrode, partly taken apart, in plan view.

In FIG. 3, a further reference electrode is shown, designed as a planar redox reference electrode made by thick-film technology. A plastic film forms a first wall part 102, onto which a current lead-off 104 in the form of a graphite conductor track is printed by the known technique of screen printing. Disposed over that is a round adhesive film 106, 0.5 mm thick, for example of the type known as Scotch 471M, which forms a framelike spacer. This spacer is provided with stamped cutouts that define both a half-cell region 108 and a current bridge region 110 and are separated from one another by a middle rib 112. A slotlike recess 114 in the middle rib acts as a primary junction, which is provided in order to form an electrochemical contact between the half-cell region 108 and the current bridge region 110. Another slotlike recess 116 in the spacer forms a measurement junction to form an electrochemical contact between the current bridge region 110 and an external measurement medium. To avoid or reduce convection, the slotlike recesses 114, 116 would have to have a very slight slot width, which however intrinsically places stringent demands in terms of production. It is more advantageous for the slotlike recesses to be filled with a convection-inhibiting material, such as a porous material, as a result of which slot widths that are substantially easier to handle can be used. If desired, the slotlike recesses can be equipped with a highly compacted filling, as a result of which convection is essentially prevented. The half-cell region 108 contains a redox half cell, which is formed by the lead-off element 104 and by a suitable redox system, such as a Red/Ox dissolved in a gel electrolyte. The current bridge region 110 contains a suitable bridge electrolyte, such as a gel-like suspension of potassium chloride. A cover film, for example a plastic film, not shown in FIG. 3 is pressed onto the adhesive film 106 and forms a second wall part 118. At least one of the two wall parts, 102 or 118, spaced apart essentially in plane-parallel fashion (e.g., spaced on opposing sides of spacer 106) is, at least in a portion bordering on the half-cell region 108, embodied as a flexible wall region, by means of which a pressure equalization without convection through the primary junction 114 is assured. The reference electrode shown in FIG. 3 can be installed in a protective housing if needed. If desired, the reference electrode can also be embodied as a "triple-junction electrode", or in other words can be equipped with a further current bridge.

Figure 4:
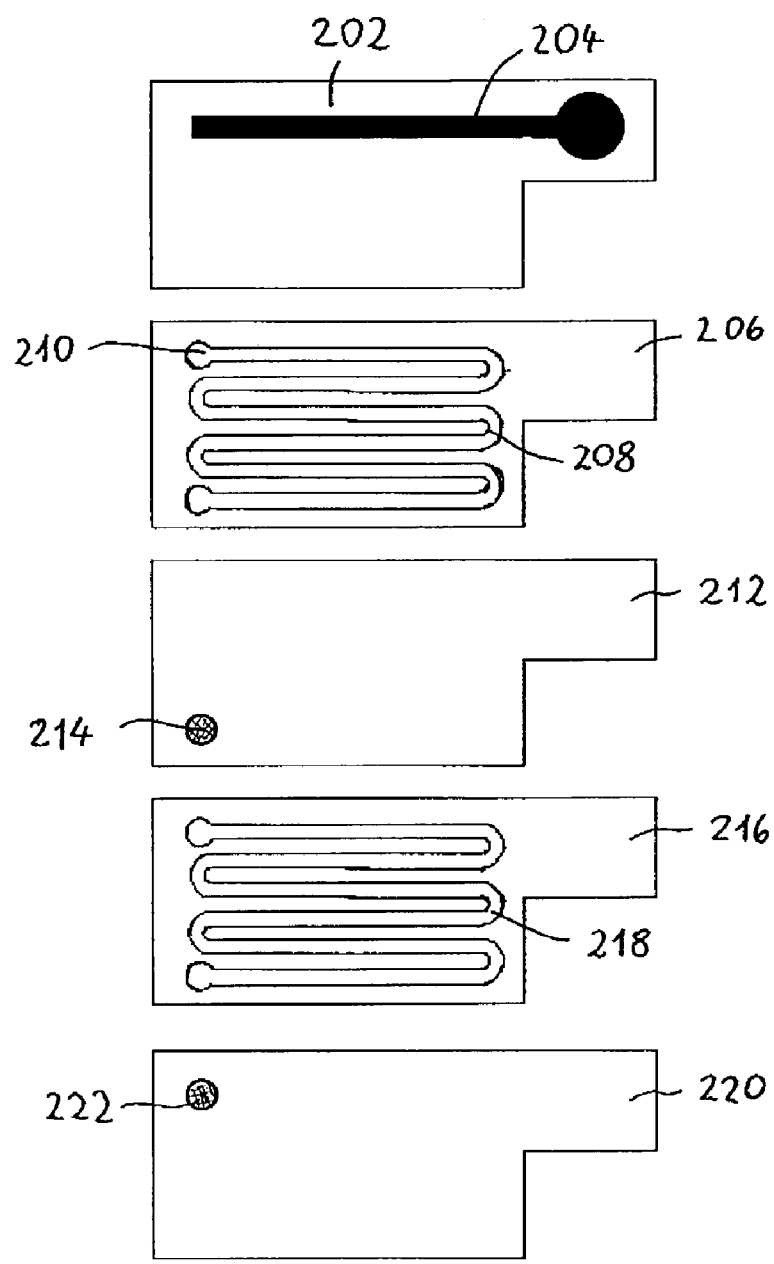
FIG. 4, a kit for an exemplary reference electrode, in longitudinal section.

FIG. 4 shows a kit for a further embodiment of a reference electrode, in which the individual components, beginning with the one shown topmost in FIG. 4, are to be placed in stacks on one another in the order given and glued together by suitable means, such as Scotch 471M adhesive film. The voids in the reference electrode are advantageously already filled during assembly; a syringe is well suited for this purpose.

A bottom film 202, for instance of mylar, is provided with a printed-on graphite conductor track 204 intended as a lead-off element. A half-cell block 206 is placed over it and contains a long, meandering recess 208 intended as a half-cell chamber. This recess comes to rest with a first end 210 above the conductor track 204 and serves to receive a suitable redox system that can be in the form of a gel-like solution and/or suspension. Next, an intermediate block 212 is put in place on it, forming an upper closure of the half-cell chamber. A first through bore 214, which is filled with a porous material and is located in the intermediate block 212, discharges into the distal part, relative to the lead-off element 204, of the meandering recess 208 and forms a primary junction of the reference electrode. Onto the arrangement described thus far, a current bridge block 216 is now put in place, which is embodied identically to the half-cell block 206 and which in particular has a meandering recess 218 acting as a current bridge chamber. This recess is intended to receive a suitable current bridge electrolyte. Finally, as the upper closure, a cap part 220 is put in place on top. As FIG. 4 shows, the cap part 220 is provided with a second through bore 222, also filled with a porous material, that is offset from the first through bore 214 of the intermediate block in such a way that the two bores discharge into different ends of the meandering recess 218. The second through bore 212 is intended as a measurement junction of the reference electrode, in order to make an electrochemical contact between a measurement medium and the current bridge electrolyte. While in the stacked arrangement described above a single half-cell block 206 and current bridge block 216 each are provided, it is easily possible instead of one of each of these individual blocks to provide a plurality of blocks stacked on one another that each contain one meandering recess, with suitably embodied intermediate blocks. In this way, the diffusion path defined by the meandering recesses can be effectively multiplied in its length.

In the example shown, the bottom film 202 forms a flexible wall region, by means of which a pressure equalization without convection through the primary junction 214 is assured. Besides mylar, so-called semi-elastic flexible materials such as soft polyolefins and the like are suitable for the bottom film 202, since in the filmlike embodiment, in contrast to a half-cell chamber embodied in the form of a hose, a pressure equalization can also be achieved with materials that are less flexible.

The exemplary embodiments described should be understood solely as examples in terms of their shape, design and dimensions. One skilled in the art will also make use as needed of modified embodiments that are based on the same principles.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. A pressure-resistant reference electrode for electrochemical measurements, comprising:
   a half cell;
   a primary current bridge for closing an electrochemical contact between the half cell and a measurement medium, which current bridge contains a primary electrolyte, wherein the half cell has both a reference electrolyte and a lead-off element, dipped into the reference electrolyte, which are disposed in a half-cell chamber that is provided with a primary junction leading to the primary current bridge and is otherwise embodied as medium-proof, the half-cell chamber having a flexible wall region which is embodied such that a pressure difference between the primary current bridge and the half cell can be compensated for essentially without convection through the primary junction; and
   two wall parts, spaced apart essentially in plane-parallel fashion, which are disposed on a framelike spacer located between them, at least one of the wall parts being formed by a film that forms the flexible wall region, the spacer being divided by a middle rib into a half-cell region and a current bridge region, and the primary junction being formed by a recess in the middle rib that is equipped with a convection- inhibiting filling.

2. A pressure-resistant reference electrode for electrochemical measurements, comprising:
   a half cell;
   a primary current bridge for closing an electrochemical contact between the half cell and a measurement medium, which current bridge contains a primary electrolyte. wherein the half cell has both a reference electrolyte and a lead-off element, dipped into the reference electrolyte, which are disposed in a half-cell chamber that is provided with a primary junction leading to the primary current bridge and is otherwise embodied as medium-proof, the half-cell chamber having a flexible wall region which is embodied such that a pressure difference between the primary current bridge and the half cell can be compensated for essentially without convection through the primary junction; and
   a plurality of stacked components, of which an outer component forms the flexible wall region of the half-cell chamber.

3. The reference electrode of claim 2, wherein the lead-off element is embodied as a conductor track.

4. The reference electrode of claim 2, wherein the half-cell chamber and/or the primary current bridge is embodied in meandering form, in order to lengthen a diffusion path between the measurement medium and the half cell.

5. The reference electrode of claim 2, wherein an electrolyte located in the electrode is in gel form.

6. The reference electrode of claim 2, wherein the flexible wall regions is formed by a film.

7. A pressure-resistant reference electrode for electrochemical measurements comprising:
   a half cell
   a primary current bridge for closing an electrochemical contact between the half cell and a measurement medium, which current bridge contains a primary electrolyte, wherein the half cell has both a reference electrolyte and a lead-off element, dipped into the reference electrolyte, which are disposed in a half-cell chamber that is provided with a primary junction leading to the primary current bridge and is otherwise embodied as medium-proof, the half-cell chamber having a flexible wall region which is embodied such that a pressure difference between the primary current bridge and the half cell can be compensated for essentially without convection through the primary junction; and
   wherein the primary junction is embodied as a compacted junction.

8. The reference electrode of claim 7, wherein the half-cell chamber is disposed inside the primary current bridge.

9. The reference electrode of claim 8, wherein the primary junction is formed by a diaphragm lined with a hydrophyllic layer.

10. The reference electrode of claim 8, wherein the primary junction is formed by an ion conducting polymer stopper or a semipermeable membrane.

11. The reference electrode of claim 7, wherein the primary junction is formed by a diaphragm lined with a hydrophillic layer.

12. The reference electrode of claim 10, wherein nonporus the diaphragm forms the flexible wall region.

13. The reference electrode of claim 11, wherein the half-cell chamber contains a secondary current bridge, disposed between the half cell and the primary junction, in which a secondary electrolyte is located and between the half cell and the secondary current bridge, a secondary junction is provided.

14. The reference electrode of claim 12, wherein the flexible wall region is disposed at the secondary current bridge.

15. The reference of claim 13, wherein the flexible wall region is formed by a hose.

16. The reference electrode of claim 7, wherein the half-cell chamber contains a secondary current bridge, disposed between the half cell and the primary junction, in which a secondary electrolyte is located, and between the half cell and the secondary current bridge, a secondary junction is provided.

17. The reference electrode of claim 7, wherein the flexible wall region is formed by a hose.

18. The reference electrode of claim 16, wherein the hose material of the flexible wall region has a maximum hardness of 70 (Shore A).

19. The reference electrode of claim 7, wherein an electrolyte located in the electrode is in gel form.

20. The reference electrode of claim 7, wherein the primary junction is formed by an ion conducting polymer stopper or a semipermeable membrane.

21. The reference electrode of claim 20, wherein the ion conducting polymer stopper or the semipermeable membrane forms the flexible wall region.

22. A pressure-resistant reference electrode for electrochemical measurements, comprising:

a half cell; and a primary current bridge for closing an electrochemical contact between the half cell and a measurement medium, which current bridge contains a primary electrolyte, wherein the half cell has both a reference electrolyte and a lead-off element which are disposed in a half-cell chamber, the half-cell chamber having a primary junction leading to the primary current bridge, the half-cell chamber having a flexible wall region which is configured to compensate a pressure difference between the primary current bridge and the half cell, wherein the primary junction is embodied as a compacted junction.

* * * * *